US00PP22472P3

(12) United States Plant Patent
Bagdasarian

(10) Patent No.: US PP22,472 P3
(45) Date of Patent: Jan. 31, 2012

(54) STRAWBERRY PLANT NAMED 'SWEET ANN'

(50) Latin Name: *Fragaria×ananassa*
Varietal Denomination: Sweet Ann

(75) Inventor: Jimmy Haig Bagdasarian, Santa Cruz, CA (US)

(73) Assignee: Lassen Canyson Nursery, Redding, CA (US)

( * ) Notice: Subject to any disclaimer, the term of this patent is extended or adjusted under 35 U.S.C. 154(b) by 0 days.

(21) Appl. No.: 12/655,174

(22) Filed: Dec. 24, 2009

(65) Prior Publication Data

US 2011/0162119 P1 Jun. 30, 2011

(51) Int. Cl.
*A01H 5/00* (2006.01)

(52) U.S. Cl. ..... Plt./208

(58) Field of Classification Search ..... Plt./208, Plt./209

See application file for complete search history.

*Primary Examiner* — Susan McCormick Ewoldt
(74) *Attorney, Agent, or Firm* — Catherine Ashley Straight

(57) ABSTRACT

A new and distinct variety of strawberry plant named 'Sweet Ann.' This new day-neutral strawberry variety is characterized by vigorous plants which produce high yields of large to very large, sweet fruit with an excellent flavor; well-shaped, long and conical fruit, having a glossy medium red exterior and medium red interior; and which plants maintain an open architecture.

6 Drawing Sheets

Latin name of genus and species: *Fragaria×ananassa.*
Variety denomination: 'Sweet Ann'.

BACKGROUND OF THE INVENTION

The present invention relates to a new and distinct variety of strawberry named 'Sweet Ann.' This new day-neutral strawberry variety is the result of a controlled cross in an ongoing breeding program made by the inventor, Jimmy Bagdasarian, in 2005. Said cross was between a strawberry variety designated '4A28,' a female, and a strawberry variety designated '10B131,' a male, in the ongoing breeding program. Pollen taken from a '10B131' plant pollinated a female '4A28' plant bearing flowers with no anthers. The flowers were covered so that no other pollen could contaminate the procedure. The variety is botanically known as *Fragaria× ananassa.*

The aforementioned controlled cross was carried out in a breeding program at Santa Cruz, Calif., USA. Strawberries developed, were later harvested and the seeds resulting from this cross were extracted and germinated in a greenhouse at Redding, Calif., USA. The resulting seedlings were transplanted to Shastina, Calif. in 2006, and grown for an additional period of time. The seedlings were asexually propagated by stolons in breeding plots in late September to Mid-October in: Irvine, Calif.; Oxnard, Calif.; Santa Maria, Calif.; and Watsonville, Calif. The new variety, designated '16F29,' was selected at Irvine, Calif. (Orange County) in 2007 from among various sibling genotypes as the 29th selection, and later named 'Sweet Ann.'

The new variety has also been "meristemed": small pieces of plant buds (approximately 0.5 mm in diameter) consisting of the undifferentiated meristem tissue and one or two leaf primordia were removed from the buds on crowns of young daughter plants, and then placed on nutrient medium and new plants grown from them. Planting stock from "meristemed" plants are growing in a screenhouse located in Redding, Calif.

The new variety was further asexually propagated by stolons in Macdoel, Calif. (Siskiyou County), Shasta County, and Manteca, Calif. (San Joaquin County). The propagules of 'Sweet Ann' ('16F29') are identical to the original plant in all distinguishing characteristics; accordingly, the propagation has demonstrated that the traits disclosed herein remain fixed and true to type through successive generations of asexual reproduction.

SUMMARY OF THE INVENTION

Sweet Ann is a day-neutral variety exhibiting the following combination of characteristics, which have been observed repeatedly and which distinguish this strawberry plant as a new and distinct variety:

1. The variety produces large to very large sized fruit;
2. The fruit is generally well shaped, long and conical;
3. The fruit is attractive, having a glossy medium red exterior and medium red interior;
4. The fruit has a good acid-sugar balance, is sweet tasting, with an excellent flavor;
5. The variety produces few runners in the fruiting field;
6. The variety exhibits high productivity of fruit; and
7. The plants are vigorous and maintain an open architecture.

The primary market for the 'Sweet Ann' variety is fresh market sales of the fruit. 'Sweet Ann' produces large sized, moderately firm berries that have an excellent flavor. The berries produced by the 'Sweet Ann' variety are also sweet tasting, a very important characteristic for fresh fruit. Table 1 shows a comparison of the Brix levels of 'Sweet Ann' as compared with 'Albion' and 'San Andreas' varieties. The sugar levels of each of the varieties were measured with a refractometer on Nov. 11, 2009, and are set forth in degrees Brix (°Bx).

TABLE 1

| Data Sample No. | °Bx 'Sweet Ann' | °Bx 'Albion' | °Bx 'San Andreas' |
|---|---|---|---|
| 1 | 13.0 | 11.0 | 7.0 |
| 2 | 12.1 | 11.0 | 10.0 |
| 3 | 11.9 | 11.2 | 5.75 |
| 4 | 10.5 | 11.6 | 8.2 |
| 5 | 13.2 | No Data | No Data |

'Sweet Ann' possesses other characteristics that are also commonly sought by commercial strawberry growers. The early fruit can be picked with petioles attached and sold as long stemmed berries. "Long stems" are prized as a very special ingredient in some dessert recipes, and typically bring a premium price. In addition, 'Sweet Ann' berries retain their firmness, color and quality even following long distance shipment.

The following Table 2 evidences the superior production of 'Sweet Ann' as compared to 'Ventana,' 'Camarosa,' 'Albion,' and 'Palomar.' Data was collected in Irvine, Calif. from Dec. 12, 2008 through Mar. 2, 2009, to calculate the average weight in grams per berry, and the average number of crates of berries produced per acre, for each of the varieties.

TABLE 2

| Variety | Average Grams per Berry | Average Crates Per Acre |
|---|---|---|
| 'Sweet Ann' | 33 | 2617 |
| 'Ventana' | 36 | 1741 |
| 'Camarosa' | 29.4 | 1984 |
| 'Albion' | 28 | 1803 |
| 'Palomar' | 36.3 | 1895 |

BRIEF DESCRIPTION OF THE DRAWINGS

The accompanying color photographs, identified as FIGS. 1 through 6, show the appearance of typical specimens of the new strawberry variety, initially designated '16F29,' and now named 'Sweet Ann.' These Figures depict the colors, as nearly true as it is reasonably possible given differences in color illustrations of this character. Accordingly, color in the photographs may differ slightly from the colors discussed in the botanical description. The photographs of the depicted plant, plant parts, and fruit of 'Sweet Ann' were taken in August of 2009.

Figure 1:
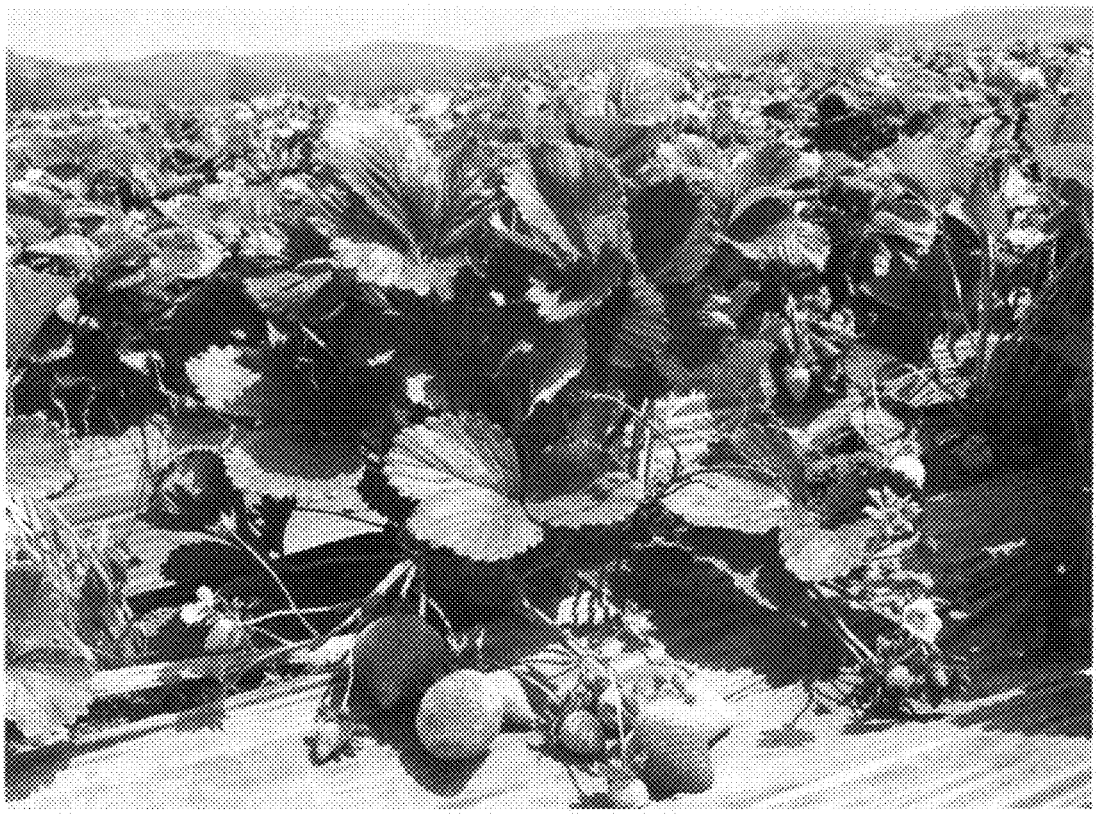
FIG. 1 shows typical fruiting and field characteristics of 'Sweet Ann'.
Figure 2:
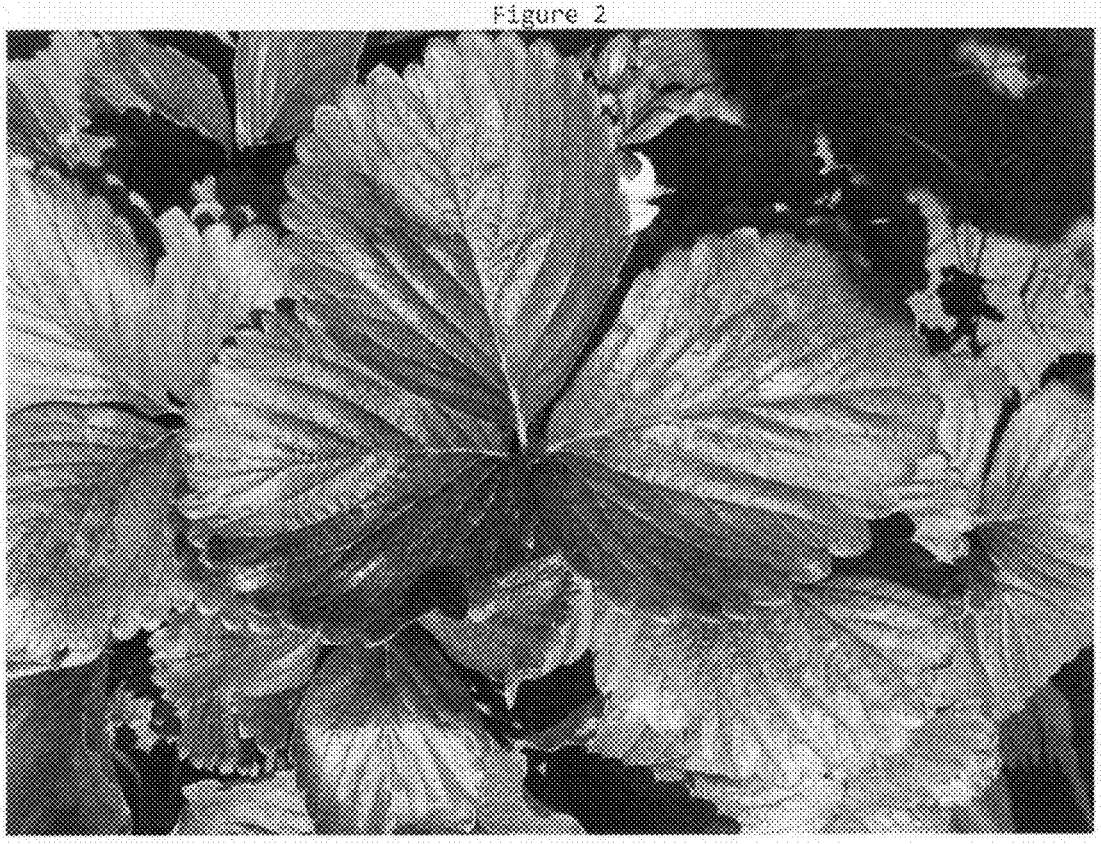
FIG. 2 shows a close up view of a typical leaf structure of 'Sweet Ann'.
Figure 3:
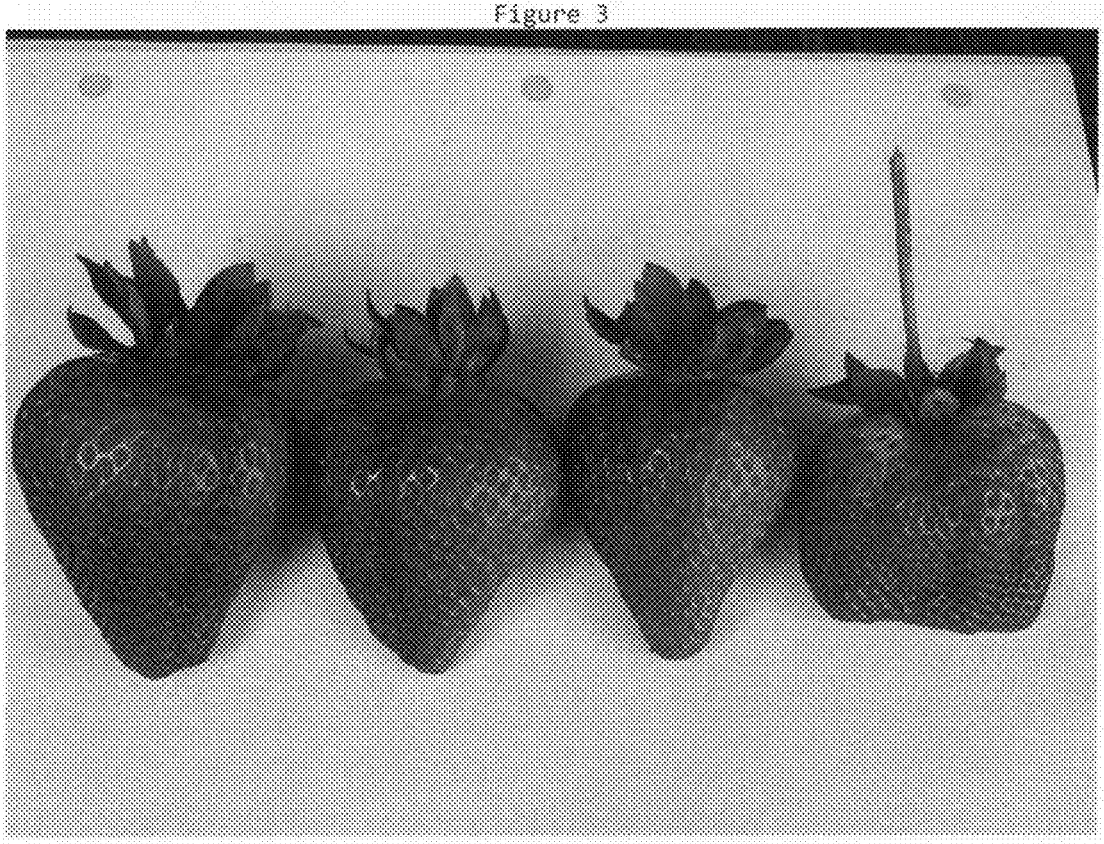
FIG. 3 shows a close up of a selection of typical mid-season fruit of 'Sweet Ann'.
Figure 4:
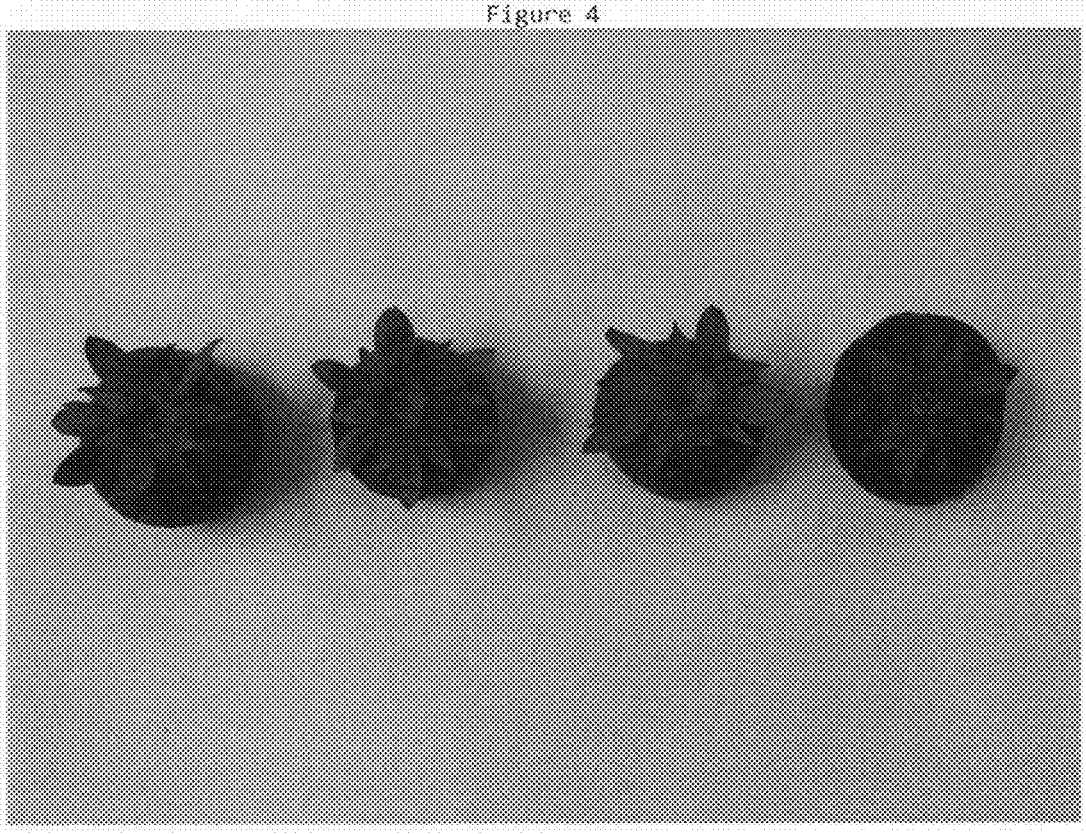
FIG. 4 shows a close up of a selection of typical mid-season calyx of 'Sweet Ann'.
Figure 5:
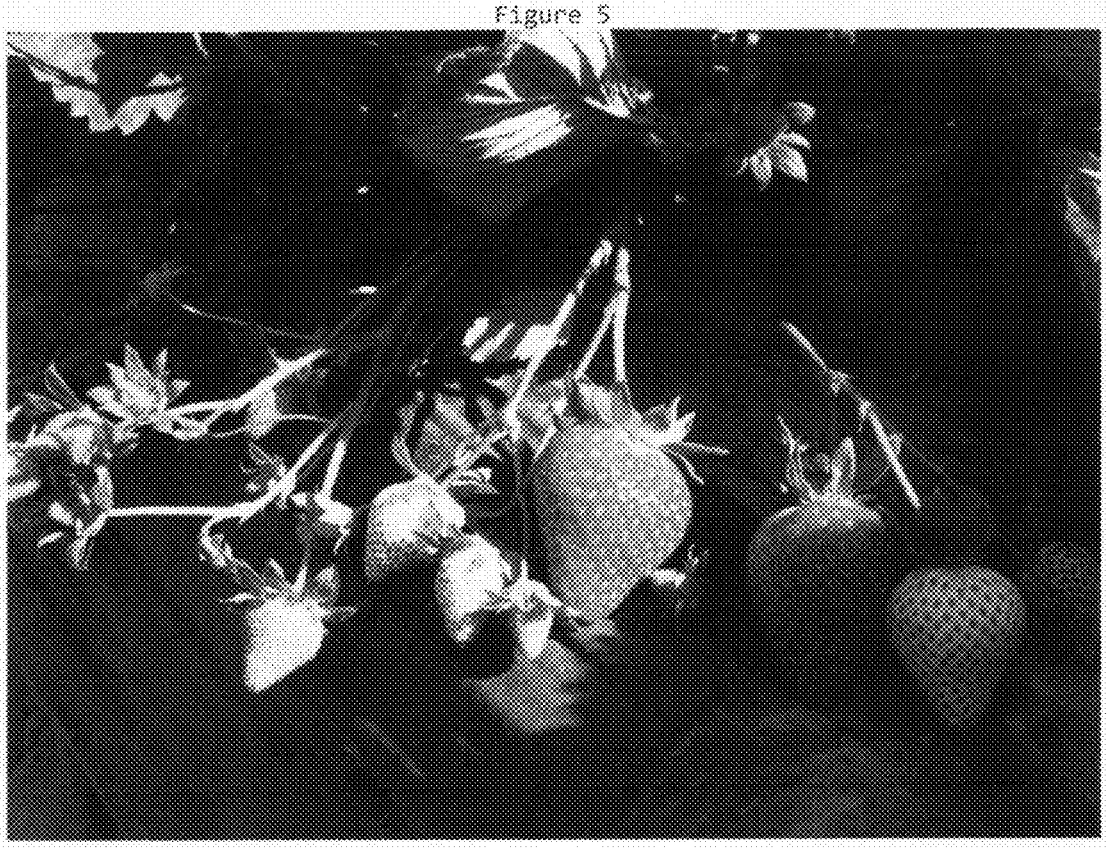
FIG. 5 shows typical mid-season fruiting trusses of 'Sweet Ann' with mature and immature fruit; and, FIG. 6 shows typical mid-season interiors of 'Sweet Ann' fruit.
Figure 6:
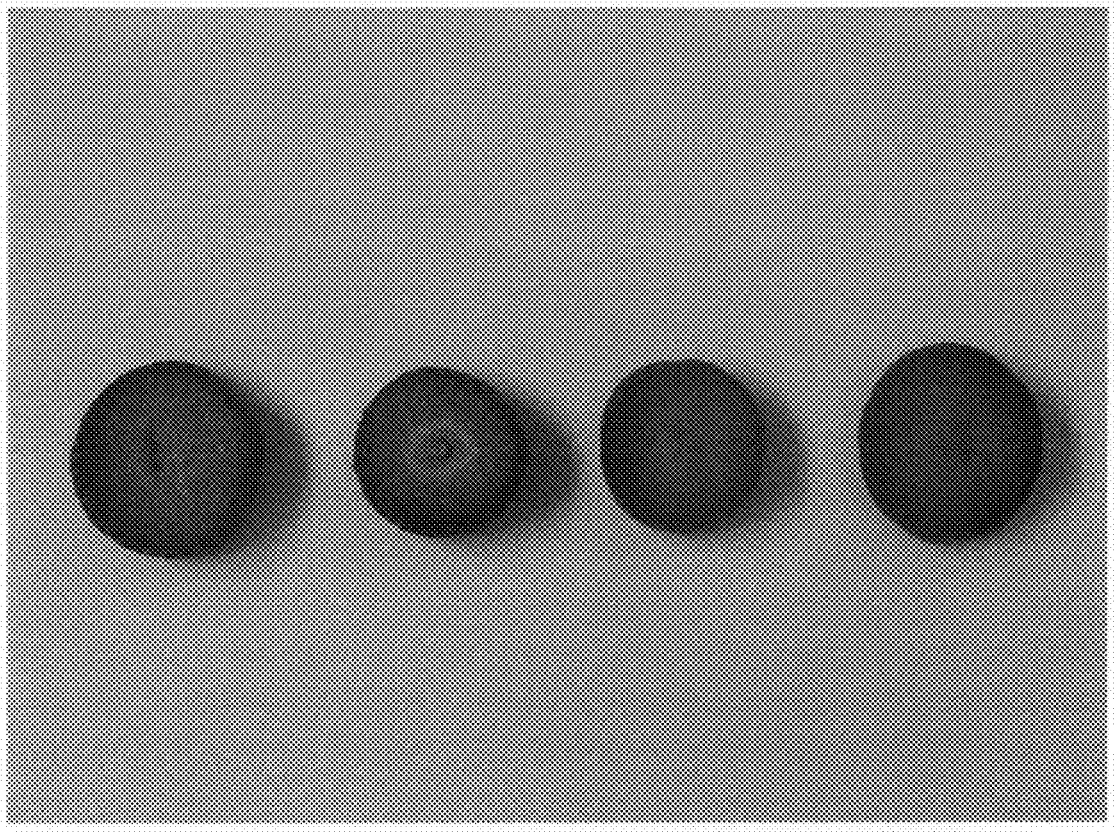

Leaf samples from three (3) plants of the the variety initially designated as '16F29,' and later named 'Sweet Ann,' were submitted for analysis to a lab for allelic fingerprint. Each of the three (3) allelic fingerprints, from the three (3) leaf samples submitted, was the same as compared to each other. Upon analysis, '16F29' was shown by allelic fingerprinting to be distinct and unique compared to the lab's large database of allelic fingerprints.

DETAILED BOTANICAL DESCRIPTION OF THE PLANT

'Sweet Ann' is the result of a cross between a strawberry variety designated '4A28' and a strawberry variety designated '10B131.' The female parent, '4A28,' is an unreleased proprietary variety having the following plant characteristics: strongly day-neutral; small size; globose habit; open density; and low plant vigor. The male parent, '10B131,' is an unreleased proprietary variety having the following plant characteristics: medium day-neutral; globose habit; tight density; and medium plant vigor. The resulting variety, named 'Sweet Ann,' has the following characteristics: weak day-neutral; large size; globose habit; open density; and high plant vigor.

The new variety was asexually propagated by stolons as described above. 'Sweet Ann' has not been observed under all possible variants in growing conditions, such as temperature, moisture, humidity, light intensity, day length, soil type and geographical location. Thus, the variety may differ in detail depending upon variance in these or other environmental factors.

Independent test plot work was done in Irvine, Oxnard, Santa Maria, and Watsonville, Calif. In these trials, evaluation of the new variety included: yield and yield distribution; fruit size, shape and overall appearance; external and internal fruit color; color and size of plant and plant parts; fruit shelf life; sweetness and fruit flavor; tolerance to disease and rain damage; and plant architecture. The description below is based upon observations of plants which were asexually reproduced by stolons, and were planted outdoors in late April in Macdoel, Calif.

TABLE 3

| Characteristics Of 'Sweet Ann' | | |
|---|---|---|
| GENUS/ SPECIES: | *Fragaria* x*Ananassa* | |
| PLANT: | Type | Day Neutral |
| | Configuration | Globose and open plant density. |
| | Vigor | Strong |
| | Parents | '4-A-28' (Female) and '10-B-131' (Male) |
| | Height | 380 mm |
| | Width | 67 mm |
| | Disease Tolerance | No formal testing of tolerance to disease has been conducted; however, in field observations, based upon performance and appearance, 'Sweet Ann' exhibits very high tolerance to disease. |
| FOLIAGE: | Size | The terminal leaflets are greater in length than width and display an average 67 mm in width and approximately 83 mm in length |
| | Margin | Commonly crenate. |
| | Shape | Orbicular. |
| | Base | Obtuse. |
| | Cross-Section | Moderately concave. |
| | Blistering | Absent or very weak. |
| | Glossiness | Medium. |
| | Color | Adaxial Surface: green 364U<br>Abaxial Surface: green 370U |
| | Petiole Texture | Medium pubescence with hairs directed outward. |
| | Petiole Color | Green 383U |
| | Petiole Length | 220 mm |
| | Petiole Height | 380 mm |
| | Leaflet Petiole | 4.25 mm average with range of 1.8 to 8.39 mm |

TABLE 3-continued

| Characteristics Of 'Sweet Ann' | | |
|---|---|---|
| | Stipule | Commonly anthocyanin coloration is absent or very weak |
| | Stipule | Adaxial color 350U; Abaxial color 371U |
| | Stipule Width | 43.25 mm average with range of 38.86 to 47.98 mm |
| | Stipule Length | 95.51 mm average with range of 76.38 to 117.49 mm |
| | Stolons | Weak presence. |
| | Stamens | mean number 30.6 |
| INFLOR-ESCENCE: | Flowering Time | Early |
| | Date of Bud Burst, Bloom Time and Duration | |
| | Southern California | November 1st to removal from field |
| | Central California | December 1st to removal from field |
| | Northern California | January 1st to removal from field |
| | Position | Approximately at or above canopy height. |
| | Length | Average length of fruiting clusters in mid-season plants is 33 cm. |
| | Petals | Average 5.4 petals that are overlapping |
| | Petal Length | Average 13.9 mm, range 12.38 to 14.98 mm |
| | Petal Width | Average 13.05 mm, range 12.28 to 13.89 mm |
| | Petal Color | Pantone white 11-0104 TPX |
| | Calyx | Color adaxial 364U and abaxial 370U that are larger in size relative to the corolla. |
| FRUIT: | Bearing | Remontant. |
| | Shape | Generally conical and occasional wedge-shaped and commonly the length is greater than the width. |
| | Length | Approximately 49.4 mm on average. |
| | Achenes | Approximately level with the fruit surface. |
| | Glossiness | Strong. |
| | External Color | Red 185C |
| | Internal Color | Red 1788C |
| | Fruit Center | Commonly solid with some hollowness. |

'Sweet Ann' differs from the parent varieties in several important characteristics including those shown in Table 4 below.

TABLE 4

Comparison of 'Sweet Ann' Characteristics to Parent Varieties

| | 'Sweet Ann' | '4A28' Female Parent | '10B131' Male Parent |
|---|---|---|---|
| Day-Neutralness | Weak day-neutral | Strongly day-neutral | Medium day-neutral |
| No. Stamens (mean). | 30.6 | 22.8 | 22.9 |
| No. Petals (mean) | 5.4 | 5.1 | 5.6 |
| Calyx Color adaxial | 364U | 370U | 370U |
| Calyx Color abaxial | 370U | 363U | 364U |
| Leaf Color adaxial | 364U | 364U | 370U |
| Leaf Color adaxial | 370U | 357U | 363U |
| Inflorescence Length | 33 cm | 24 cm | 31 cm |
| Plant Configuration | Globose Large open density | Globose Small open density | Globose Tight density |
| Plant Vigor | High | Low | Medium |

'Sweet Ann' is distinguished by its production of large to very large fruit of exceptional flavor, medium skin firmness and medium red to full red external color. Contrast is made to 'Albion' (U.S. Plant Pat. No. 16,228) and 'Aromas' (U.S. Plant Pat. No. 10,451), as well as other commercially grown varieties as indicated in the tables below. High productivity, sweetness, and exceptional flavor of the fruit, along with vigorousness of the plant, make this new variety highly competitive in the strawberry industry.

The leaf and fruit color of 'Sweet Ann' is readily distinguished from that of other commercially grown strawberry varieties. Table 5 shows the visually observed characteristics of 'Sweet Ann' leaf and fruit colors as compared to leaf and fruit color characteristics of 'Chandler,' 'Camarosa,' 'Albion,' and 'Catalina.' Color terminology where noted herein is in accordance with the Pantone Color Formula Guide GP 1201.

TABLE 5

Comparison of 'Sweet Ann' Leaf and Fruit Colors

| Variety Name | Color Adaxial Leaf | Color Abaxial Leaf | Color External Fruit | Color Internal Fruit |
|---|---|---|---|---|
| 'Sweet Ann' | 364U | 370U | 185C | 1788C |
| 'Chandler' | 343C | 339U | 186C | 179C |
| 'Camarosa' | 349C | 348U | 193C | 185C |
| 'Albion' | 357U | 74900 | n/a | n/a |
| 'Catalina' | 343C | 349U | 193C | 185C |

In Table 6, a comparison of the mid-tier leaf width, mid-tier leaf length, petiole length, and plant height between 'Sweet Ann' ('16F29') and the varieties 'Albion' and 'Aromas' is shown.

TABLE 6

Comparison of Foliar Characteristics of 'Sweet Ann' to 'Albion' and 'Aromas'

| Foliar Characteristic (expressed in mm) | | 'Sweet Ann' | 'Albion' | 'Aromas' |
|---|---|---|---|---|
| Mid-tier Leaf Width: | Mean | 67 | 73 | 92 |
| | Range | 52-88 | 50-95 | 67-100 |
| Mid-tier Leaf Length: | Mean | 83 | 68 | 74 |
| | Range | 70-104 | 50-95 | 65-85 |
| Petiole Length: | Mean | 220 | 135 | 156 |
| | Range | 150-280 | 105-170 | 135-200 |
| Plant Height: | Mean | 380 | 252 | 257 |
| | Range | 290-480 | 210-270 | 230-330 |

Tables 7 and 8 show, respectively, a comparison of certain foliar and flower petal characteristics between 'Sweet Ann' and the varieties 'Diamante' and 'Aromas.'

TABLE 7

Comparison of Foliar Characteristics of 'Sweet Ann' to 'Diamante' and 'Aromas'

| Foliar Characteristic | 'Sweet Ann' | 'Diamante' | 'Aromas' |
|---|---|---|---|
| Plant Height (mm) | 380 | 231 | 257 |
| Plant Width (mm) | 67 | 73 | 92 |
| Petiole Length (mm) | 220 | 149 | 156 |
| Leaf Convexity | moderately concave | some flat, most slightly concave | some flat, most slightly concave |
| Leaf Pubescence | Moderate | Very Light | Moderate |

TABLE 8

Comparison of Flower Petals of 'Sweet Ann' to 'Diamante' and 'Aromas'

| | 'Sweet Ann' | 'Diamante' | 'Aromas' |
|---|---|---|---|
| Petal Number (mean) | 5.4 | 5.4 | 5.7 |
| Petal Length (mean) (mm) | 13.9 | 13.4 | 13.8 |

TABLE 9

| Results | |
|---|---|
| Lab No: 911589-25491 | |
| Date received: Aug. 26, 2009 | |
| Date reported: Sep. 9, 2009 | |
| Received as: | Strawberry, |
| Lot(s): | 16F29 |
| Qty tested: | 3 samples |
| Test ID 1252 | Variety ID by DNA markers |
| Strawberry variety ID | |
| Sample submitted by: Jim Bagdasarian | |
| Analysis: Leaf samples from 3 plants were analyzed. | |

TABLE 9-continued

| Results | | |
|---|---|---|
| # | Submitted as | Result |
| 1 | 16F29 | New - added to database |
| 2 | 16F29 | 16F29 |
| 3 | 16F29 | 16F29 |
| Allelic fingerprint (base pairs): | | |
| Marker 54: 204, 206, 229 | | |
| Marker 60: 190, 216, 232 | | |
| Marker 55: 235, 245, 265 | | |

I claim:

1. A new and distinct strawberry plant named 'Sweet Ann' as herein described and illustrated by the characterizations set forth above.

* * * * *